United States Patent [19]
Blankenship et al.

[11] Patent Number: 5,233,977
[45] Date of Patent: Aug. 10, 1993

[54] ANESTHESIA/BREATHER BAG WITH A ROUGHENED EXTERIOR SURFACE

[75] Inventors: Tommy Blankenship, Roanoke, Va.; Robert S. Crook, Littleton, Colo.; Walter J. Morris, Oklahoma City, Okla.

[73] Assignee: Marquest Medical Products, Inc., Englewood, Colo.

[21] Appl. No.: 823,070

[22] Filed: Jan. 14, 1992

Related U.S. Application Data

[63] Continuation of Ser. No. 473,675, Feb. 2, 1990, abandoned.

[51] Int. Cl.⁵ .............................................. A62B 7/00
[52] U.S. Cl. .............................. 128/205.13; 128/205.17
[58] Field of Search ................ 425/93, 275, 269, 270, 425/272, 271, 273, 274, 417; 249/65; 264/340, 232, 233, 301, 305, 306, 314, 318, 341, 49; 128/205.13, 205.17, DIG. 24

[56] References Cited

U.S. PATENT DOCUMENTS

| | | | |
|---|---|---|---|
| 1,472,256 | 10/1923 | Stringfield | 425/269 |
| 2,064,143 | 12/1936 | Belton et al. | 264/307 |
| 2,525,272 | 10/1950 | Rhoton | 264/307 |
| 2,568,128 | 9/1951 | Morris | 264/301 |
| 2,614,561 | 10/1952 | Fox | 128/205.17 |
| 3,072,914 | 1/1963 | Velonis et al. | 425/69 |
| 3,356,100 | 12/1967 | Seeler | 128/205.13 |
| 3,363,833 | 1/1968 | Laerdal | 128/205.13 |
| 3,689,613 | 9/1972 | Talalay | 264/306 |
| 4,061,709 | 12/1977 | Miller et al. | 264/305 |
| 4,501,545 | 2/1985 | Divoky | 425/275 |
| 4,517,987 | 5/1985 | Sackner et al. | 128/719 |
| 4,532,923 | 8/1985 | Flynn | 128/205.13 |
| 4,945,918 | 8/1990 | Abernathy | 128/719 |

FOREIGN PATENT DOCUMENTS 624453 9/1961 Italy ................... 128/205.13

Primary Examiner—David A. Wiecking
Assistant Examiner—Aaron J. Lewis
Attorney, Agent, or Firm—Sheridan Ross & McIntosh

[57] ABSTRACT

A breather bag (10) is adapted for use with a breathing circuit (12). The exterior surface (38) of the bag (10) is roughened and substantially non-uniform for ease of gripping by an anesthesist (18). When the gloves (33) of the anesthesist (18) are wet, the gloves (33) tend to cause slippage when attempting to squeeze a bag as known in the prior art. Due to the present invention, the roughened exterior surface (38) greatly reduces this likelihood of slippage. A relatively small exterior portion (40) is substantially smooth as is the interior surface (46).

3 Claims, 1 Drawing Sheet

ANESTHESIA/BREATHER BAG WITH A ROUGHENED EXTERIOR SURFACE

This application is a division of U.S. Application Ser. No. 07/473,675 by Blankenship et. al., filed Feb. 2, 1990, now abandoned and entitled "ANESTHESIA/BREATHER BAG WITH A ROUGHENED EXTERIOR SURFACE."

TECHNICAL FIELD OF THE INVENTION

This invention relates in general to medical products, and in particular to an anesthesia/breather bag having a roughened exterior surface for ease of handling with a gloved hand.

BACKGROUND OF THE INVENTION

In the operating room environment, it is important to prevent cross-contamination between the patient and other personnel. With the increased advent of readily communicable and fatal diseases such as AIDS, the use of protective gowns, masks and gloves has become essential.

In a typical operation in which a patient is to be anesthetized, there is a myriad of equipment which must be handled by doctors, nurses and other operating room personnel. As is to be expected, the operating room personnel may become contaminated with bodily fluids from the patient, for example, blood may accumulate on the gloved hands of any of these personnel. Once a surgical glove is contaminated with a fluid, such as blood, the operating room personnel may encounter difficulty in picking up or holding objects. Since a steady grip is generally required in the manipulation of many pieces of operating room equipment, personnel may have a tendency to remove their protective gloves to properly manipulate the piece of equipment. Removal of surgical gloves or other protective gear creates a risk of the spread of contamination from the operating room personnel to the patient, as well as from the patient to the operating room personnel.

An example of such a potential problem exists with the use of an anesthetic/breather bag (hereinafter referred to as a breather bag) attached to a breathing machine such as, for example, an anesthetic machine. The anesthetic machine combines oxygen for breathing with an appropriate anesthetic for maintaining the unconscious state of the patient. On such a machine, there is a circuit generally comprising a plurality of tubes for the passage of mixed gases from a source through various other devices (such as an absorber cannister and a humidifier) to the patient. Typically, a breather bag is attached to the circuit to hang freely therefrom in a vertical orientation. The breather bag is provided as a supplemental supply of gas to allow the anesthesist some manual control over patient ventilation. The bag preferably has a 1-3 liter volume for use with adults (other sizes being possible for children).

The breather bag is generally constructed of an elastomeric material such as latex capable of being inflated and deflated repeatedly. The exterior surface of the breather bag is generally smooth-surfaced as a result of the latex "dip" method of manufacture. The latex "dip" method requires the use of a mandrel having the shape of the product to be formed. The mandrel is dipped into a liquid supply of latex which collects on the mandrel to form the product. The mandrel is then removed along with the product formed thereon to cure or harden.

In the use of the anesthesia machine, a facial mask is typically attached to the patient end of the circuit for initial delivery of the anesthetic gas to the patient. Once the patient is unconscious, it is preferable to remove the facial mask and insert an endotracheal tube. Prior to removal of the mask, the anesthesist or one of the operating room personnel will inflate the lungs of the patient by squeezing the breather bag several times to pump extra oxygen and anesthetic into the patient. The mask will then be removed, and an endotracheal tube will be inserted into the patient. The patient end of the anesthetic machine must then be connected to the endotracheal tube, and the patient will once again typically be provided with several pumps of oxygen and anesthetic from the breather bag. The patient will then be maintained by the automatic aspects of the anesthetic machine to be supplemented by the breather bag.

As previously indicated above, if the anesthesist or other operating room personnel have surgical gloves that have become contaminated with blood or other fluids, the breather bag will also become contaminated with the fluids. The vertically orientated bag then may become slippery enough that a secure grip thereon is difficult to attain. The operating room personnel may then remove their surgical gloves to obtain a secure grip and pump the breather bag. Once the surgical gloves have been removed, the personnel have subjected themselves to the possibility of contamination. This contamination may then be transmitted from the hand of the person who has pumped the bag to other personnel and other equipment in the operating room.

It is known in the art that the exterior surface of breather bags has some inherent tackiness, as disclosed in U.S. Pat. No. 3,556,097 to Wallace, Jan. 19, 1971. The tacky exterior surface provides some protection against slipping when both the gloved hand and the bag are clean and dry. However, as is known in the art, the bags are usually provided with a light coating of corn starch to reduce the tendency of the bags to stick together during shipping and while being stored. Thus, the inherent tackiness of the external surface is compromised by the corn starch unless washed off. If the corn starch is removed by washing (and assuming the bag is dried) the inherent tackiness of the bag is restored until the bag is contaminated with bodily fluids. Thus, the inherent tackiness of the breather bag exterior surface is insufficient to prevent slippage once the surface becomes wet.

One possible alternative to removing the surgical gloves is to replace the breather bag with a reduced volume version of the bag. A smaller bag allows a person with a wet gloved hand to encircle the bag for a better grip. Unfortunately a smaller bag may not provide sufficient oxygen to the patient without further adjustments (more squeezes) and is thus generally not an acceptable alternative. Therefore, it is desirable to provide a way to reduce the likelihood of cross contamination and specifically to prevent the need for removal of a surgical glove to use a breather bag.

In a non-analogous art, heavy industrial, chemical and electrical gloves, have been provided with roughened exterior surfaces. The roughened exterior surface is formed on the gloves using a mandrel "dip" technique. A mandrel having the shape of the glove is first coated with the material from which the glove is made. Then, prior to allowing the glove to cure or dry, the coated mandrel is dipped into a tank containing an acid or other solution which reacts with the glove material. The reaction between the glove material and the solution results in an uneven and therefore roughened exterior surface on the gloves.

A roughened exterior surface is advantageous when, for example, if a chemical handler wearing such gloves is working with chemicals, the gloves will become contaminated on the exterior surfaces thereof with the chemical. If the handler subsequently desires to do another task such as lift a chemical drum, the wet gloves may slip on the drum. For the sake of safety and to reduce such slipping, the gloves are provided with a roughened exterior surface. The rough surface provides extra contact between the glove and the object being gripped and, therefore, reduces the likelihood of slippage.

However, in the medical equipment art, there is no similarly roughened surgical glove. This is due to the fact that a surgeon needs to have protection against contaminants without loss of dexterity and "touch" of the hands. The roughening of surgical gloves would likely require the use of a thicker glove reducing the surgeon's "touch" and is therefore undesirable. Thus, there is a need for a breather bag with a roughened exterior surface that will allow operating room personnel to manipulate even when wearing a surgical glove contaminated with bodily fluids.

SUMMARY OF THE INVENTION

The present invention disclosed herein comprises an anesthesia/breather bag with a roughened exterior surface which substantially reduces problems associated with prior anesthesia/breather bags. The present invention allows the gripping and manipulating of the bag with a gloved hand without slippage.

In accordance with one aspect of the invention, a breathing circuit includes a gas monitoring machine for receiving a gas to be analyzed by the machine. At least one circuit tube communicating with the patient carries gas to and from the patient. An improved breather bag, connected to the circuit tube, is adapted to be gripped by a person wearing a glove having substantially smooth exterior finger surfaces. The bag is provided with a roughened, substantially non-uniform exterior surface. A person is thus able to grip the breather bag even when using substantially smooth exterior surfaced gloves without a substantial likelihood of slippage.

In another aspect of the present invention, the roughened, substantially non-uniform exterior surface is formed on a substantial majority of the exterior surface of the breather bag. A relatively small, substantially smooth portion is disposed at an end of the breather bag attached to the circuit. The interior surface of the breather bag is substantially smooth and uniform. The breather bag extends substantially vertically from the circuit, and the roughened surface thereon thus substantially prevents slippage of the gloved hand from around the bag as well as in a substantially vertical direction.

It is a technical advantage of the present invention that operating room personnel are able to grip a breather bag without substantial slippage. The roughened exterior surface of the bag improves the contact between the bag and the substantially smooth finger surfaces of a surgical glove when the bag and/or the glove are wet. Thus, operating room personnel will not have a tendency to remove their gloves to obtain sufficient grip on the breather bag. It is a further technical advantage that the present invention will reduce the likelihood of spreading contamination in the operating room.

BRIEF DESCRIPTION OF THE DRAWINGS

For a more complete understanding of the present invention and for further advantages thereof, reference is now made to the following Detailed Description taken in conjunction with the accompanying Drawings, in which.

DETAILED DESCRIPTION OF THE INVENTION

Figure 1:
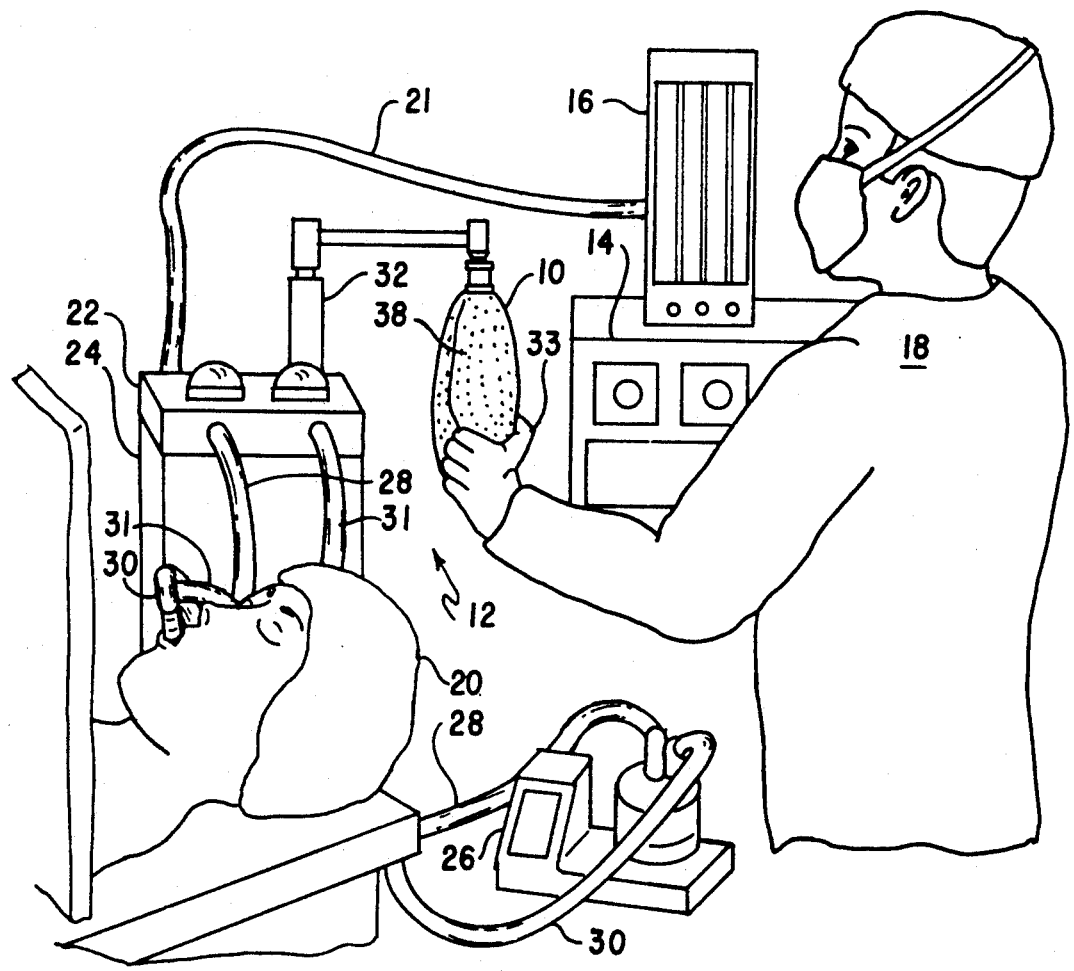
FIG. 1 is a perspective view of a typical operating room environment in which the present invention is utilized.

Referring first to FIG. 1, a perspective view of a typical operating room environment in which an anesthetic/breather bag 10 (hereinafter referred to as a breather bag) is utilized. It is to be understood that the breathing circuit generally identified by the reference numeral 12 as depicted in FIG. 1 is greatly simplified for the sake of clarity and is not intended to depict a complete system. A source of gas (not shown) provides the appropriate gases, such as, for example, oxygen and nitrous oxide, to the circuit 12.

The circuit 12 is provided with a pressure monitoring station 14 and a gas flow rate monitoring station 16. The pressure monitoring station 14 allows an anesthesist 18 or other operating room personnel to ensure gas is provided to the circuit 12 at the proper pressures. The flow rate monitoring station 16 is provided to allow the anesthesist 18 to monitor and to adjust the flow rate of the various gasses to the patient 20.

A gas flow tube 21 interconnects the flow rate monitoring station 16 to an absorber cannister 22. The absorber 22 is provided to allow the conservation of expensive anesthetic gas by allowing the patient to rebreath the gases in the circuit 12. A scrubbing material 24, such as soda lime, is placed in the absorber 22 to remove the carbon dioxide from the exhaled gas to allow rebreathing thereof.

Gas flows from the absorber 22 to a humidifier 26 through a gas tube 28. The humidifier 26 provides both moisture and temperature control to the gas prior to breathing by the patient 20. The controlled gas is then passed to the patient 20 through a gas tube 30.

After the patient 20 exhales the gas, the exhaled gas is returned to the circuit 12 through a gas tube 31. The tube 31 is connected to the absorber 22 to allow the exhaled gas to be filtered by the scrubbing material 24 and eventually rebreathed by the patient 20. Thus the circuit 12 depicts a simplified version of a closed or rebreathing circuit. Although not shown, it is to be understood that the present invention is equally applicable to other types of breathing circuits such as an open or non-rebreathing circuit.

The breather bag 10 is attached to the circuit 12 by a connector 32 in a generally vertical orientation. The connector 32 interconnects the bag 10 to the $CO_2$ absorber 22 to allow a pumping of the bag 10 to force gas to the patient 20 through the absorber 22 and the humidifier 26. Thus the anesthesist 18, through the use of the bag 10, has a supplementary manual control over ventilation of the patient 20.

In operation, the anesthesist 18 uses the breather bag 10 as a supplement to the supply of gas to the patient 20.

For example, after the patient 20 has been initially anesthesized by the anesthetic gas, it is preferable to insert an endotracheal tube rather than continue the use of a facial mask. The anesthesist 18, normally wearing smooth fingered surgical gloves 33, will therefore use the bag 10 to ventilate the patient 20 by pumping several bags full of gas therein to patient. The facial mask would then be removed, an endotracheal tube inserted, and the circuit 12 reinstalled. The anesthesist 18 would again pump several bags full of gas to the patient and then allow the circuit 12 to operate automatically.

If the gloves 33 of the anesthesist 18 become wet (from bodily fluids or any other source) the bag 10 also becomes contaminated by and wet from contact with the gloves 33. Once the bag 10 becomes wet, there is a tendency for a gloved hand to slip off from around the bag when trying to grip the bag. Additionally, since the bag 10 is generally vertical, the hand may also slip vertically downward and off of the bag. Since it is necessary for the well being of the patient to pump the bag, the anesthesist 18 tends to remove the gloves 33 for a better grip.

Due to the present invention, the anesthesist is no longer inclined to remove the surgical gloves 33 in response to a slippery bag. The roughened exterior surface 38 of the bag 10 greatly reduces the likelihood of slippage due to contamination thereof from bodily or other fluids.

Figure 2:
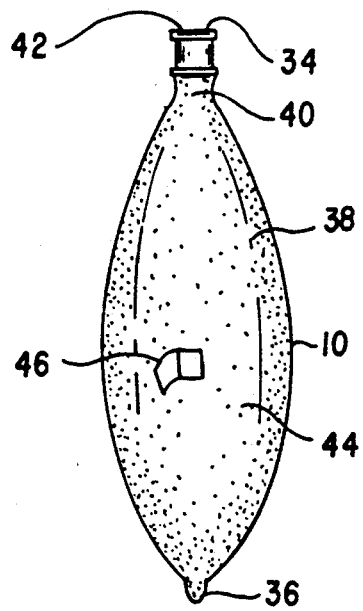
FIG. 2 is a side elevation of the present invention.

Referring to FIG. 2, a front elevation of the breather bag 10 is shown. The bag 10 is of a general contoured shape, as is well-known in the art. The internal volume of the bag 10 may vary as required for the appropriate application thereof and is generally 1-3 liters for use with an adult. An open end 34 of the bag 10 provides internal access thereto by a gas. An opposite end 36 is sealed to prevent escape of gas from other than the open end 34. As is well known in the art, the bag 10 may have a valve (not shown) to relieve pressure within the circuit 12.

In an important aspect of the present invention, the exterior surface 38 of the bag 10 is roughened and substantially non-uniform. The roughened exterior surface 38 reduces the likelihood of slippage when grasped by a surgically gloved hand even when the bag 10 and/or the gloved hand are wet.

A relatively small exterior portion 40 proximate the open end 34 is substantially smooth. As will be subsequently described in greater detail, the small portion 40 is substantially smooth due to one possible manufacturing process. Attached to the open end 34 is a connecting adapter 42 for connecting the bag 10 to a circuit such as the circuit 12 as show in FIG. 1. The connecting adapter 42 may be secured to the bag 38 by any appropriate means such as tape, adhesive or shrink wrap. As shown at the cutout portion 44, the interior surface 46 is substantially smooth and uniform.

Figure 3:
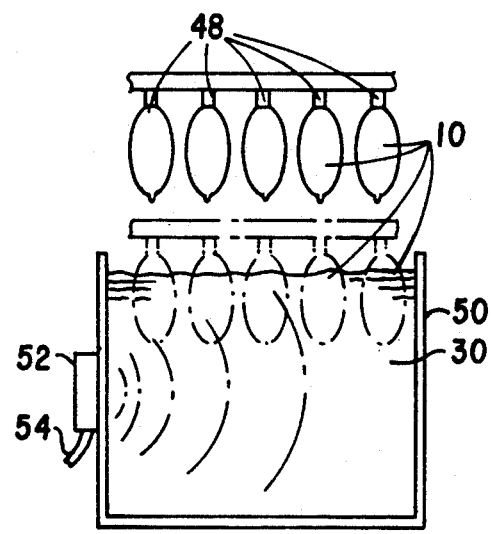
FIG. 3 is a simplified representation of a technique used for forming the breather bag of the present invention.

Referring to FIG. 3, a simplified version of a method for forming the bag 10 is illustrated. The bags 10 are first formed by dipping mandrels 48 into a liquid form of the material from which the bag 10 is formed such as, for example, latex, as is well-known in the art. The mandrels 48 are then removed from the liquid latex by any appropriate means and prior to the curing or hardening thereof are dipped into a tank 50.

The tank 50 contains a roughening agent such as a solvent or an acid solution, as is well-known in the art of making roughened industrial, chemical or electrical gloves. Just prior to dipping the coated mandrels 48 into the tank 50, the solvent or acid therein is agitated by any appropriate means such as, for example, a mechanical agitator 52 which strikes the tank 50 with a device 54. The coated mandrels 48 are then dipped into the tank 50 as indicated in dashed lines in FIG. 3. The agitation of the solvent or acid solution causes the exterior surface 38 of the bags 10 to become roughened. As is shown in FIG. 3, a portion of each bag 10 is not fully immersed in the solution and therefore forms the substantially smooth areas 40. The entire bag 10 is not fully immersed due to the desire to prevent the solution from spilling over into the interior of the bag and contaminating both the bag and the mandrel. The bags 10 are then removed from the tank 50, allowed to fully cure and are removed from the mandrels 48 for use with a circuit 12.

Although not shown it is to be understood that other techniques may be used to make the bag 10. For example, blow molding or injection molding may be used to form the bags 10 with the roughened exterior surface 38. Additionally, the exterior surface 38 of the bag 10 may be provided with ribs, cross-hatching or the like to provide a sufficiently roughened surface.

Although the present invention has been described with respect to a specific preferred embodiment thereof, various changes and modifications may be suggested to one skilled in the art, and it is intended that the present invention encompass such changes and modification as fall within the scope of the appended claims.

What is claimed is:

1. A method for making an anesthesia/breather bag for use in a medical operating room and which supplements an anesthesia machine, comprising:

providing a flexible container having an outlet end for connection to a breathing circuit, said container having a single layer that is made of substantially the same material with said single layer being substantially solid throughout;

providing a liquid roughening agent in a tank;

placing at least portions of said container in the tank;

forming a roughened exterior surface as part of said single layer using said liquid roughening agent, with said roughened exterior surface occupying substantially continuously, in both lateral and vertical directions, a majority of the entire exterior surface of said container, said forming step including agitating said liquid roughening agent wherein said exterior surface of said container becomes roughened due to said agitating step, with said agitating step including agitating of said liquid roughenign agent independent of said step of placing said portions of said container in the tank; and leaving substantially no smooth bag portion within said substantially continuously occupying roughened exterior surface during said step of forming.

2. A method, as claimed in claim 1, wherein:

said step of agitating includes applying a force to said tank during one of: before said portions of said container are placed in the tank and while said portions of said container are placed in the tank.

3. A method, as claimed in claim 1, wherein:

said step of forming includes creating substantially the same degree of roughness throughout all of said roughened exterior surface.

* * * * *